United States Patent
Kang et al.

(10) Patent No.: US 11,407,694 B2
(45) Date of Patent: Aug. 9, 2022

(54) METHOD FOR DECOMPOSING BYPRODUCTS IN PHENOL PRODUCTION PROCESS

(71) Applicant: LG CHEM, LTD., Seoul (KR)

(72) Inventors: Min Suk Kang, Seoul (KR); Sang Beom Lee, Seoul (KR); Sung Ho Lee, Seoul (KR); Joon Ho Shin, Seoul (KR); Chul Han Park, Seoul (KR)

(73) Assignee: LG CHEM, LTD., Seoul (KR)

( * ) Notice: Subject to any disclaimer, the term of this patent is extended or adjusted under 35 U.S.C. 154(b) by 224 days.

(21) Appl. No.: 16/478,802

(22) PCT Filed: Aug. 17, 2018

(86) PCT No.: PCT/KR2018/009459
§ 371 (c)(1),
(2) Date: Jul. 17, 2019

(87) PCT Pub. No.: WO2019/098501
PCT Pub. Date: May 23, 2019

(65) Prior Publication Data
US 2021/0130256 A1    May 6, 2021

(30) Foreign Application Priority Data

Nov. 20, 2017   (KR) .......................... 10-2017-0154969

(51) Int. Cl.
*C07C 1/20* (2006.01)
*C07C 37/52* (2006.01)
*C07C 45/82* (2006.01)

(52) U.S. Cl.
CPC ............. *C07C 1/20* (2013.01); *C07C 37/52* (2013.01); *C07C 45/82* (2013.01)

(58) Field of Classification Search
CPC . C07C 1/20; C07C 37/52; C07C 45/82; Y02P 20/10
See application file for complete search history.

(56) References Cited

U.S. PATENT DOCUMENTS 3,850,996 A * 11/1974 Nixon, Jr. ............... C07C 37/74
                                                                568/754
4,158,611 A    6/1979 Cooke
(Continued)

FOREIGN PATENT DOCUMENTS

CN      1125250 A    6/1996
EP      0008869 A1   3/1980
(Continued)

OTHER PUBLICATIONS

Konstantinos et al., "Design of Sidestream Distillation Columns", Industrial and Engineering Chemistry Process Design and Development, vol. 24., No. 3., pp. 822-828 (1985).

*Primary Examiner* — Rosalynd A Keys
(74) *Attorney, Agent, or Firm* — Dentons US LLP

(57) ABSTRACT

In a process of decomposing byproducts of a phenol production process using a reactive distillation column in which a reactor and a distillation column are integrated, since acetophenone is mixed with tar recovered to a lower part of the reactive distillation column and transferred, viscosity of the tar may be lowered so that the tar may be transferred at room temperature, and since the reactive distillation column may be operated at 0.5 to 3 bar, an operating temperature of the reactive distillation column is low as compared with a method of separating acetophenone by pressurization with high pressure, significantly reducing an operation cost of a heater required for a reaction. Also, since acetophenone is separately recovered at a position of 25 to 90% of a total
(Continued)

number of stages in the reactive distillation column, recovery of an active ingredient may be enhanced.

7 Claims, 3 Drawing Sheets

(56) References Cited

U.S. PATENT DOCUMENTS

| | | | |
|---|---|---|---|
| 4,246,203 A | | 1/1981 | Wirth |
| 5,240,568 A | | 8/1993 | Chan et al. |
| 5,283,376 A | | 2/1994 | Dyckman et al. |
| 5,457,244 A | * | 10/1995 | Dyckman ............... C07C 37/86 |
| | | | 568/754 |
| 6,025,530 A | | 2/2000 | Dyckman et al. |
| 6,965,056 B1 | | 11/2005 | Taggart et al. |

FOREIGN PATENT DOCUMENTS

| | | | | |
|---|---|---|---|---|
| EP | 0168358 A1 | | 1/1986 | |
| EP | 3628655 A1 | | 4/2020 | |
| JP | 52-35656 B1 | | 9/1977 | |
| JP | 60-123434 A | | 7/1985 | |
| JP | 1999021562 A | | 1/1999 | |
| JP | H1121562 A | * | 1/1999 | ............. C07C 37/52 |
| JP | 2011500831 A | | 1/2011 | |
| JP | 2016517846 A | | 6/2016 | |
| KR | 960014083 A | | 5/1996 | |
| KR | 100161038 B1 | | 8/1998 | |
| KR | 20000073225 A | | 12/2000 | |
| KR | 100665764 B1 | | 12/2006 | |
| KR | 1020110134075 A | | 12/2011 | |
| WO | 2009080338 A1 | | 7/2009 | |

\* cited by examiner

METHOD FOR DECOMPOSING BYPRODUCTS IN PHENOL PRODUCTION PROCESS

CROSS-REFERENCE TO RELATED APPLICATIONS

This application is the U.S. national stage of international application No. PCT/KR2018/009459, filed on Aug. 17, 2018, and claims priority under 35 U.S.C. § 119 to Korean Application No. 10-2017-0154969, filed on Nov. 20, 2017, whose entire disclosures are herein incorporated by reference.

TECHNICAL FIELD

The present disclosure relates to a method for decomposing byproducts generated in a phenol production process, and more particularly, to a method for decomposing byproducts to improve thermal efficiency in terms of process and recovery of an active ingredient in a phenol production process.

BACKGROUND ART

About 95% of phenol used worldwide is generally produced by a three-step Hock process. The 3-step Hock process comprises (1) alkylating benzene with propylene to form cumene, (2) bonding cumene with oxygen to oxidize cumene to cumene hydroperoxide (CHP), (3) and decomposing CHIP into phenol and acetone under the presence of a sulfuric acid catalyst. In the cumene oxidizing step, byproducts such as acetophenone (AP), dimethylbenzyl alcohol (DMBA), dicumylperoxide (DCP), and dicumylum (DC), and the like, in addition to the CHIP, are produced, and in the CHIP decomposing step, hydroxyacetone (HA), 2-methylbenzofuran (2MBF), alpha-methylstyrene (AMS), mesityl oxide (MO), alpha-methylstyrene dimer (AMS dimmer), cumylphenol (CP), and the like, are produced as byproducts.

In a stream in which phenol, acetone, and various byproducts generated through the above reaction process are mixed, an unreacted cumene, acetone, AMS, HA, and the like, are separated as the top of an acetone column and the phenol, some AMS, 2MBF, and other impurities, and the like, are separated as the bottom. The phenol mixture separated as the bottom is introduced into a phenol column so that impurities such as DCP, CP, AMS dimer, and tar are separated and removed as the bottom.

Many studies have been conducted to increase a yield and purity of useful products contained in impurities in the recovery step of the tar of the impurities.

DISCLOSURE

Technical Problem

An object of the present disclosure is to provide a method for decomposing byproducts in a phenol production process to improve recovery of an active ingredient contained in byproducts in a phenol production process and lower energy required for a decomposition reaction of the byproducts.

Another object of the present disclosure is to provide a byproduct decomposition apparatus capable of effectively decomposing byproducts in a phenol production process.

Technical Solution

In one general aspect, a method for decomposing phenol byproducts produced in a phenol production process includes: supplying the phenol byproducts to a reactive distillation column; recovering tar from a lower part of the reactive distillation column; recovering acetophenone from the middle of the reactive distillation column; and recovering an active ingredient from an upper part of the reactive distillation column.

The reactive distillation column may be operated under the condition of 0.5 to 3 bar.

The method may further include: mixing the recovered acetophenone with the tar.

The method may further include: exchanging heat between the mixed stream of the tar and the acetophenone and the phenol byproducts supplied to the distillation column to heat the phenol byproducts.

The active ingredient may include phenol, alpha methyl styrene, and cumene.

The acetophenone separated from a side part in the middle of the reactive distillation column may be 90 wt % or more of the acetophenone contained in the phenol byproducts, and the content of acetophenone contained in the active ingredient recovered from the upper part of the reactive distillation column may be 1 wt % or less of the content of the entire recovered active ingredient.

Here, the percentage may refer to wt %, unless otherwise mentioned.

In another general aspect, an apparatus for decomposing phenol byproducts includes: a phenol byproduct supply part for supplying byproducts of a phenol production process to a reactive distillation column; a tar recovery part provided at a lower part of the reactive distillation column; a tar transfer line transferring tar recovered from the tar recovery part; an acetophenone recovery part provided at a middle part of the side of the reactive distillation column; an acetophenone transfer line connected to the tar transfer line to mix the acetophenone recovered from the acetophenone recovery part with the recovered tar; and an active ingredient recovery part provided at an upper part of the reactive distillation column.

The acetophenone recovery line may be provided at a position of 25 to 90% of a total number of stages of the reactive distillation column.

The decomposition apparatus may further include: a heat-exchanger exchanging heat between a mixed stream of the recovered tar and acetophenone and the phenol byproducts.

Advantageous Effects

In the process of decomposing phenol byproducts using a decomposition apparatus (reactive distillation column) in which a reactor and a distillation column are integrated, acetophenone contained in the phenol byproducts is separated at normal pressure and mixed with tar recovered to the lower part of the reactive distillation column and transferred, whereby viscosity of the tar may be lowered so that the tar may be transferred at room temperature, and since acetophenone is separated at normal pressure, operation energy of the distillation column may be lowered as compared with a pressurizing process. Also, since the acetophenone recovery part is separately provided at the position of 25 to 90% of the total number of stages of the distillation column, acetophenone may be effectively separated from the active ingredient.

BEST MODE

The present disclosure may be modified variably and may have various embodiments, particular examples of which will be illustrated in drawings and described in detail herein. However, it is to be understood that the present disclosure is not limited to a specific embodiment but includes all modifications, equivalents, and substitutions without departing from the scope and spirit of the present disclosure. In describing embodiments of the present disclosure, when a detailed description of known techniques associated with the present disclosure is determined to unnecessarily obscure the gist of the present disclosure, the detailed description will be omitted.

Generally, in order to decompose phenol byproducts produced in a phenol production process, the phenol byproducts are introduced into a reactor and a distillation column, and an active ingredient (alpha methyl styrene, phenol, cumene, etc.), acetophenone (AP), and tar are separately recovered.

Figure 1:
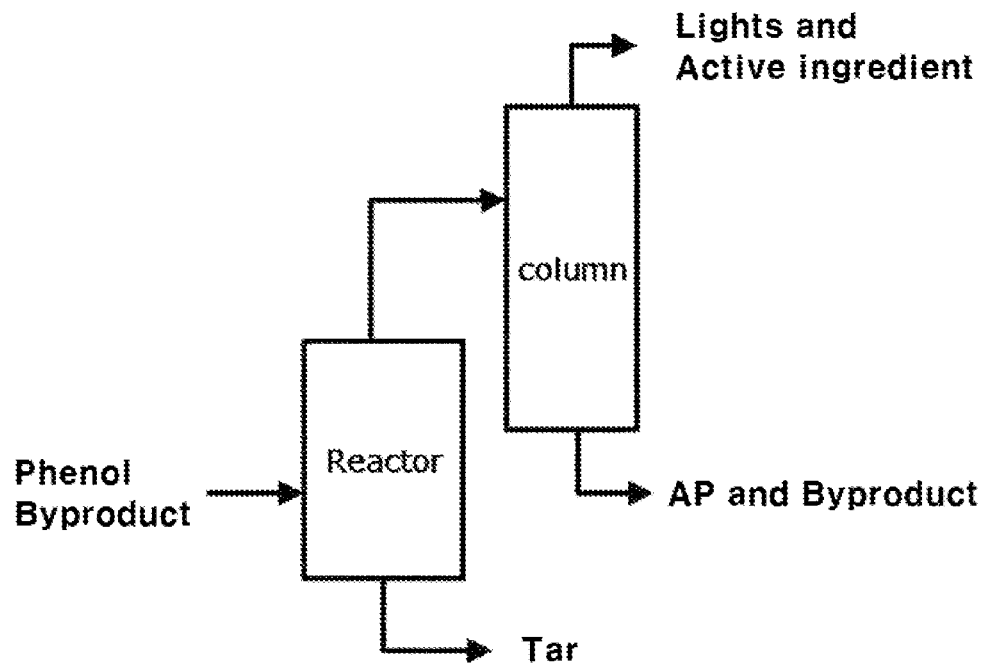
FIG. 1 schematically illustrates the related art phenol byproduct decomposition apparatus (Comparative Example 1) in which a reactor and a distillation column are separated.

For example, as illustrated in FIG. 1, in a type in which the reactor and the distillation column are separated, tar is primarily recovered to a lower part of the reactor, and the component containing the active ingredient and AP (acetophenone) are recovered to an upper part of the reactor and subsequently pass through the distillation column so as to be separated as the active ingredient and AP.

Figure 2:
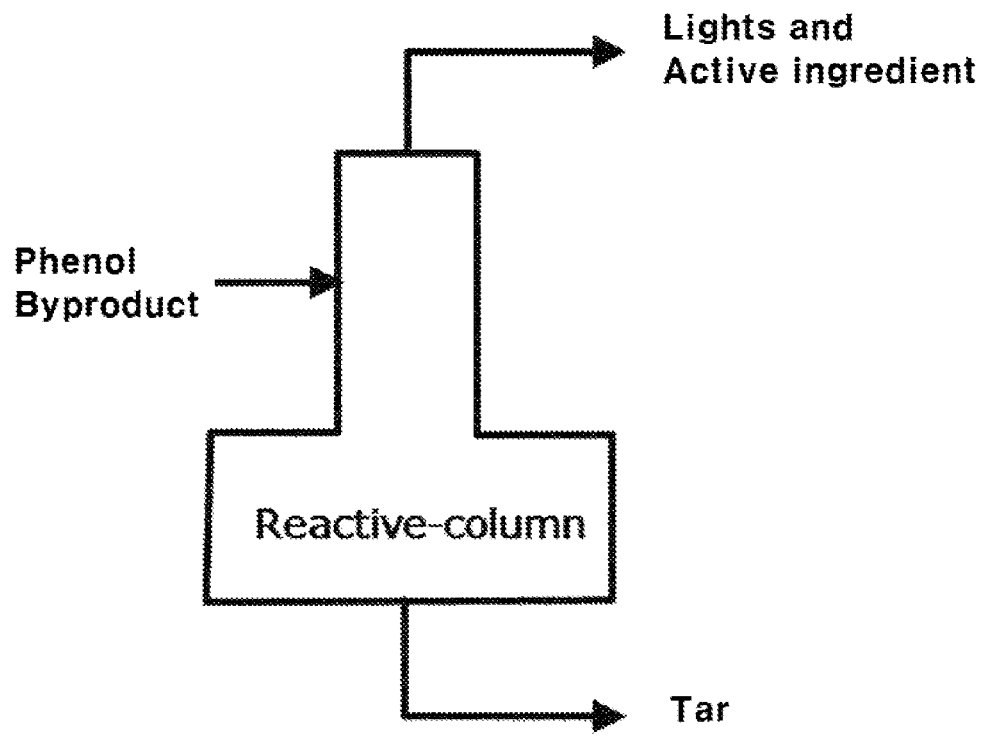
FIG. 2 schematically illustrates the related art phenol byproduct decomposition apparatus (Comparative Example 2) in which a reactor and a distillation column are integrated.

Alternatively, as illustrated in FIG. 2, in the case of the reactive distillation column type in which the reactor and the distillation column are integrated, a method of recovering tar from the lower part of the reactive distillation column, increasing a boiling point of AP by applying pressure to the inside of the reactive distillation column, and subsequently separately recovering the active ingredient and AP. However, when AP is separated by pressing as described above, the possibility of dimerization and polymerization of alpha methyl styrene (AMS) contained in the active ingredient may increase and the dimerized and polymerized AMS may be discharged in a state of being included in the tar due to a high boiling point.

In order to solve the problem of the related art, the present disclosure provides a method for decomposing phenol byproducts, including: supplying the phenol byproducts to a reactive distillation column; recovering tar from a lower part of the reactive distillation column; recovering acetophenone from a middle part of the side of the reactive distillation column; and recovering an active ingredient from an upper part of the reactive distillation column, in a process of decomposing the phenol byproducts produced in a phenol production process.

According to an embodiment, the method may further include: mixing the recovered acetophenone with the tar.

Here, the "reactive distillation column" refers to a distillation column in which a reactor and a distiller are integrated. Also, "phenol byproducts" refers to byproducts produced in the phenol production process. In the present disclosure, the tar may further contain other byproducts excluding a component separated from the active ingredient recovery part after the reaction, and the active ingredient recovered from the upper part may include phenol, AMS, and cumene among products obtained as the phenol byproducts are decomposed.

Two methods may be used to separate acetophenone from the active ingredient using a reactor-distillation column integrated separating apparatus. A first method is increasing a boiling point of acetophenone by pressurization and condensing acetophenone at a specific temperature to discharge acetophenone to a lower part together with tar (FIG. 2). When acetophenone is pressurized, the boiling point of acetophenone may be increased so as to be separated together with tar, without using a separate separation line of acetophenone, but since an operational temperature in the column is increased, a large amount of heat duty is consumed, and the possibility of dimerization of AMS may be relatively increased. Also, since phenol forms azeotrope with acetophenone, phenol may be significantly lost when acetophenone is separated, lowering active ingredient recovery.

On the other hand, in the method of separating acetophenone by a reactor-distillation column integrated separating apparatus according to the present disclosure, the problem in the pressurization method may be solved by separating acetophenone under the condition of normal pressure like the separation type. In the present disclosure, an acetophenone separation line is separately provided at the side of a position of a middle part of the reactive distillation column to effectively separate acetophenone from the active ingredient under the condition of normal pressure.

According to an embodiment, the reactive distillation column may be operated at 0.5 to 3 bar, preferably, at 0.5 to 2 bar, more preferably, at 0.5 to 1.5 bar, and most preferably, at normal pressure. As a result, the operating temperature of the reactive distillation column is lowered as compared with pressurized operation, and thus, dimerization and polymerization of AMS may be suppressed.

Also, since the operating temperature is lowered, heat duty of a heater required for the process of separating the active ingredient and acetophenone may be significantly reduced as compared with the existing method.

Figure 3:
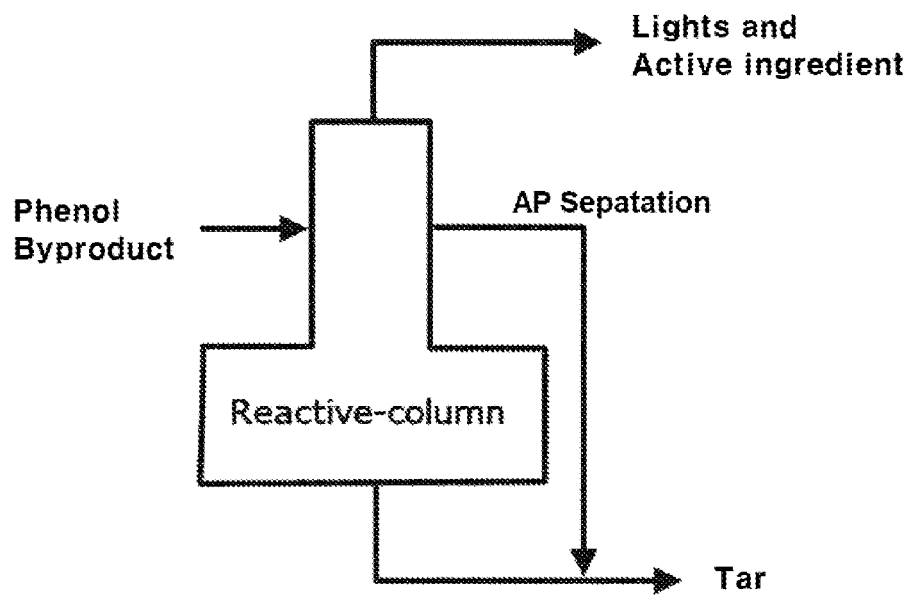
FIG. 3 schematically illustrates a configuration (Example 1) of a reactive distillation column according to an embodiment of the present disclosure.

The present disclosure provides a decomposition apparatus as illustrated in FIG. 3 in order to more efficiently perform the phenol byproduct decomposition process. Specifically, the present disclosure provides a decomposition apparatus including a phenol byproduct supply part for supplying byproducts of a phenol production process to a reactive distillation column; a tar recovery part provided at a lower part of the reactive distillation column; a tar transfer line transferring tar recovered from the tar recovery part; an acetophenone recovery line provided at a side of the middle part of the reactive distillation column; an acetophenone transfer line connected to the tar transfer line to mix the acetophenone recovered from the acetophenone recovery line with the recovered tar; and an active ingredient recovery part provided at an upper part of the reactive distillation column.

Here, the acetophenone recovery line is provided at a position of 25 to 90% of the total number of stages in the reactive distillation column, preferably, 45 to 90%, and more preferably, 50 to 90% of the total number of stages in the reactive distillation column. Here, the total number of stages refers to a position from the top of the reactive distillation column.

Also, in order to effectively use thermal energy required for the decomposition process, the present disclosure may include exchanging heat between the mixed stream of the tar and the acetophenone and the phenol byproducts supplied to the distillation column to pre-heat the phenol byproducts before being supplied to the distillation column.

Figure 4:
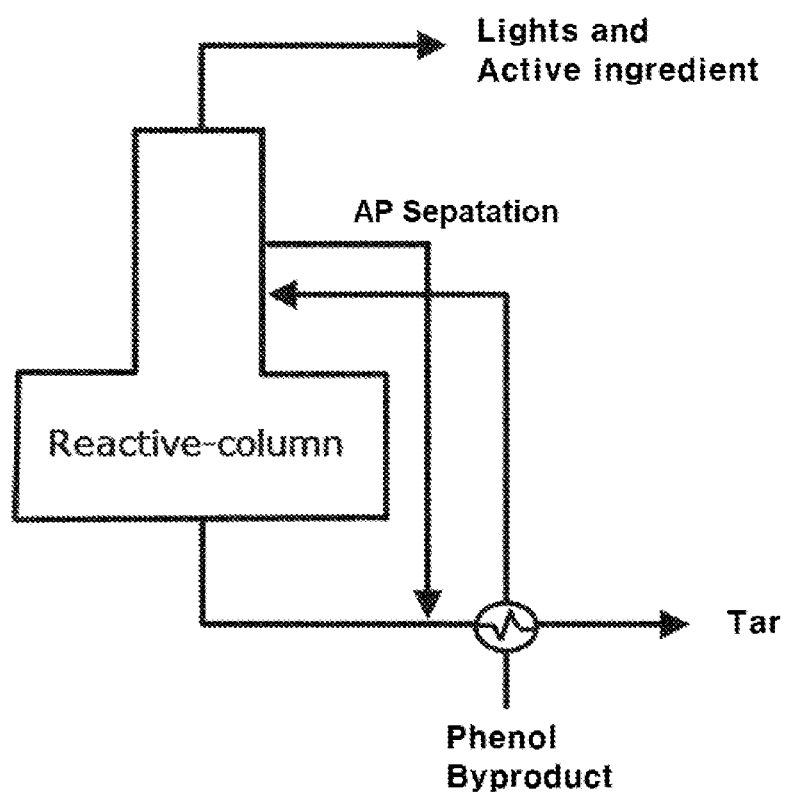
FIG. 4 schematically illustrates a configuration (Example 2) of a reactive distillation column including a heat exchanger according to another embodiment of the present disclosure.

For example, as illustrated in FIG. 4, the decomposition apparatus may further include a heat exchanger between the phenol byproduct supply part and the recovered tar and acetophenone transfer line to cause heat-exchange between the mixture of the tar and the acetophenone and the phenol byproducts.

Since the tar mixed with acetophenone may be transferred even at room temperature, thermal energy supplied from the tar recovered to the lower part of the reactor may be transferred by heat exchange with the phenol byproducts supplied to the reactive distillation column, and thus, cost for operating the heater for the reaction may be significantly reduced.

According to an embodiment, at least 90 wt % or more of acetophenone contained in the phenol byproducts may be separated from the middle part (25 to 90% of the total number of stages) of the side of the reactive distillation column, and when the separated acetophenone is mixed with tar, viscosity of the tar may be significantly lowered so that tar may be transferred and stored at room temperature.

The related art process for separating phenol byproducts has a problem in that when a temperature of the tar separated to the lower part of the reactor is lowered, viscosity thereof is significantly increased, which makes it difficult for the tar to be smoothly transferred and stored.

In general, viscosity of a fluid flowable in a transfer pipe may be about 60 Pa·s at 80° C., and viscosity of the tar at room temperature may be about 1000 Pa·s. Therefore, in order to transfer the tar using the transfer pipe used in the general process, the viscosity of the tar must be lowered to 60 Pa·s or less. Generally, in order to transfer tar, it is necessary to increase the temperature of the tar or to mix the tar with a specific material.

In order to solve the problem of transferring and storing tar at room temperature by taking advantage of the fact that viscosity of the tar may be lowered by mixing acetophenone present in the phenol byproducts with the tar, the acetophenone separated from the reactor is mixed with the tar to significantly lower the viscosity of the tar, whereby the tar may be smoothly transferred and stored even at room temperature, thus reducing energy required for the process. In the present disclosure, as for separation of the active ingredient and acetophenone, due to the characteristic that the phenol contained in the active ingredient forms azeotrope with acetophenone, it is difficult to separate 100 wt % of acetophenone from the active ingredient, and thus a small amount of acetophenone may be contained in the active ingredient recovery part, but in the process of decomposing the phenol byproducts using the reactive distillation column in which the reactor and the distillation column are integrated, acetophenone may be separated from the middle part of the side of the reactive distillation column and mixed together with the tar recovered from the lower part of the distillation column and transferred, whereby viscosity of the tar may be significantly lowered to be transferred at room temperature. Also, since acetophenone is separable at normal pressure, recovery of the active ingredient may be significantly improved as compared with the existing method of recovering acetophenone under a pressurized condition, and since an operating temperature of the reactive distillation column is low, energy required for the process may be significantly reduced.

According to an embodiment, the mixed stream of tar and acetophenone may maintain viscosity allowing smooth transfer at a temperature of 25° C. or more, and the viscosity may be gradually reduced as the temperature increases.

Viscosity of the mixed stream of tar and acetophenone may be 30 Pa·s or less at 25° C., preferably, 20 Pa·s or less, and more preferably, 10 Pa·s or less. The viscosity may be 1 Pa·s or less or 0.5 Pa·s or less depending on a mixing ratio of the tar and acetophenone and an operating temperature and may be significantly lowered to 0.3 Pa·s or less. Therefore, in the present disclosure, by mixing the tar and acetophenone to transfer the tar, the tar may be smoothly transferred even at a temperature condition of room temperature without raising the temperature. Also, the viscosity may be reduced by 10 times or more as the temperature rises.

A mixing ratio of the tar and acetophenone may be arbitrarily selected and may be varied depending on a composition of the phenol byproducts (AP content in the existing phenol byproducts) or the degree of AP separation from the active ingredient in the distillation column. For example, the tar and acetophenone may be mixed in a weight ratio of 10:1 to 1:10, and the viscosity of the mixed stream may be reduced as the mixing ratio of acetophenone increases, and in order to exhibit sufficient fluidity at room temperature, the mixing ratio of the tar and acetophenone may be 1:0.3 or greater or 1:0.4 or greater by weight ratio, and preferably, 1:0.9 or less, or 1:0.8 or less.

Hereinafter, embodiments of the present disclosure will be described in detail so that those skilled in the art may easily carry out the present disclosure. The present disclosure may, however, be embodied in many different forms and should not be construed as limited to the embodiments set forth herein.

Comparative Example 1

Phenol byproducts were decomposed using a decomposition apparatus (see FIG. 1) in which a reactor for thermal decomposition and a distillation column were separated.

Comparative Example 2

Phenol byproducts were decomposed using a decomposition apparatus (see FIG. 2) in which a reactor and a distillation column were integrated.

Example 1

Phenol byproducts were decomposed using a decomposition apparatus (see FIG. 3) in which an acetophenone recovery line connected to a tar transfer line at a lower part of a reactive distillation column in which a reactor and a distillation column were integrated is provided at a middle part of the side of the reactive distillation column (50% of the total number of stages).

Example 2

Similar to Example 1, Phenol byproducts were decomposed using a decomposition apparatus (see FIG. 4) in which an acetophenone recovery line is connected to a tar transfer line at a lower part of a reactive distillation column in which a reactor and a distillation column were integrated, and is positioned at a middle part (50% of the total number of stages) of the side of the reactive distillation column, and a heat exchanger is provided between an acetophenone-tar mixture transfer line and a phenol byproduct supply line.

Comparative Example 3

Figure 5:
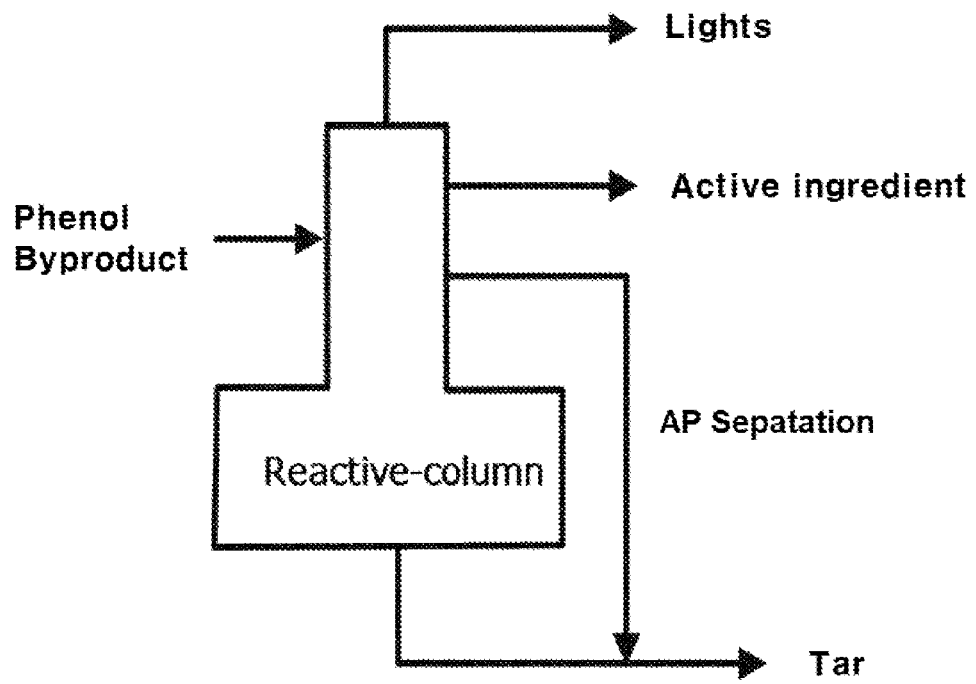
FIG. 5 schematically illustrates a configuration (Comparative Example 3) in which the related art phenol byproduct decomposition apparatus, in which a reactor and a distillation column are integrated, separates only an active ingredient from the side of a column.

Phenol byproducts were decomposed in a mode (see FIG. 5) in which an acetophenone recovery line connected to a tar transfer line at a lower part of a reactive distillation column in which a reactor and a distillation column were integrated is provided at a middle part of the side of the reactive distillation column (50% of the total number of stages) and an active ingredient was separately separated from the side (20% of the total number of stages) of the reactive distillation column.

Compositions and recovery of the active ingredients separated and recovered from the decomposition apparatuses of Comparative Examples 1 to 3 and Examples 1 and 2, pressure conditions and operating energy applied to the decomposition process are illustrated in Table 1 below.

In the case of Comparative Example 1, a space problem arises due to separate installation of the reactor and the distillation column and addition of the heater results in measurement of the highest heat duty. In the case of Comparative Example 2, a high heat duty was measured due to enhancement of the operating temperature of the reactor in accordance with the pressurization condition.

Meanwhile, in Example 2, the heat duty was minimized by providing the heat exchanger between the phenol byproducts and the tar transfer line. Based on these results, it is possible to provide a decomposition apparatus capable of further reducing heater operation cost.

Meanwhile, in the case of Comparative Example 3, it was confirmed that when only the active ingredient was separated from the side of the reactive distillation column, the recovery of the active ingredient was lowered, although it was advantageous in terms of heat duty.

While the present disclosure has been shown and described in connection with the embodiments, it will be apparent to those skilled in the art that modifications and variations may be made without departing from the spirit and scope of the invention as defined by the appended claims.

The invention claimed is:

TABLE 1

| Classification | | Phenol byproduct | Example 1 | Example 2 | Comparative Example 1 | Comparative Example 2 | Comparative Example 3 |
|---|---|---|---|---|---|---|---|
| Pressure (KG) | | — | 0.00 | 0.00 | 0.00 | 7.00 | 0.00 |
| Heat duty (Gcal/hr) | | — | 0.27 | 0.22 | 0.35 | 0.38 | 0.25 |
| Ingredient ratio of recovered active ingredient (wt %) | Phenol | 4.21 | 7.72 | 7.72 | 8.59 | 12.28 | 4.61 |
| | Alpha-methyl styrene | 7.88 | 28.85 | 28.85 | 24.48 | 7.33 | 22.40 |
| | Cumene | 0.00 | 5.56 | 5.56 | 3.53 | 6.49 | 3.90 |
| | Acetophenone | 19.22 | 0.04 | 0.04 | 0.04 | 0.04 | 0.04 |
| | Cumylphenol | 28.04 | 0.00 | 0.00 | 0.00 | 0.00 | 0.00 |
| | Dimers of alpha-methyl styrene | 15.40 | 0.00 | 0.00 | 0.00 | 0.00 | 0.00 |
| | Others | 25.25 | 1.96 | 1.96 | 1.96 | 1.95 | 0.05 |
| Total | | 100.00 | 44.13 | 44.13 | 38.60 | 28.09 | 31.00 |

* When about 99 wt % or more of AP with respect to 1000 kg/hr of phenol byproducts is mixed In the decomposition apparatuses of Examples 1 and 2 and Comparative Examples 1 to 3, the phenol byproducts were thermally decomposed to produce about 20 wt % of tar.

As illustrated in Table 1, in the decomposition methods of Examples 1 and 2 and Comparative Examples 1 to 3, about 99 wt % or more of acetophenone contained in the phenol byproducts was separated, and as in Examples 1 and 2, when acetophenone was mixed with tar, viscosity was significantly lowered, and thus, the transfer and storage problems may be solved even under the operating conditions at room temperature.

Also, it can be seen that, although about 99 wt % or more of acetophenone in the phenol byproducts was separated in all of Examples 1 and 2 and Comparative Examples 1 to 3, recovery of the active ingredients was higher in Examples 1 and 2, and this may occur because acetophenone is effectively separated as the acetophenone recovery line is provided at the position of 25 to 90% of the total number of stages in the reactive distillation column, and also, as acetophenone is separated at a low temperature, an operating temperature of the distillation column is lowered to suppress dimerization and polymerization of AMS.

1. A method for decomposing phenol byproducts produced in a phenol production process, the method comprising:
   supplying the phenol byproducts to a reactive distillation column to perform a decomposition reaction;
   recovering tar from a lower part of the reactive distillation column;
   recovering acetophenone from a middle portion of a side part of the reactive distillation column;
   mixing the recovered acetophenone with the recovered tar at room temperature at a mixing ratio of 1:0.3 to 1:0.9 to form a mixed stream of the recovered tar and the recovered acetophenone; and
   recovering an active ingredient from an upper part of the reactive distillation column.

2. The method of claim 1, wherein the reactive distillation column is operated at 0.5 to 3 bar.

3. The method of claim 1, further comprising:
   exchanging heat between the phenol byproducts supplied to the reactive distillation column and the mixed stream of the recovered tar and the recovered acetophenone to heat the phenol byproducts.

4. The method of claim 1, wherein the active ingredient comprises phenol, alpha-methylstyrene, and cumene.

5. An apparatus for decomposing phenol byproducts, the apparatus comprising:
- a phenol byproduct supply part for supplying phenol byproducts of a phenol production process to a reactive distillation column;
- a tar recovery part provided at a lower part of the reactive distillation column to recover tar;
- a tar transfer line to transfer tar recovered from the tar recovery part;
- an acetophenone recovery line provided at a middle part of a side of the reactive distillation column;
- an acetophenone transfer line connected to the tar transfer line to mix the acetophenone recovered from the acetophenone recovery line with the recovered tar; and
- an active ingredient recovery part provided at an upper part of the reactive distillation column.

6. The apparatus of claim 5, wherein the acetophenone recovery line is positioned at 25 to 90% of a total number of stages of the reactive distillation column.

7. The apparatus of claim 5, further comprising:
- a heat exchanger for exchanging heat between a mixed stream of the recovered tar and acetophenone and the phenol byproducts.

* * * * *